(12) United States Patent
Nakamura et al.

(10) Patent No.: US 10,273,197 B2
(45) Date of Patent: Apr. 30, 2019

(54) METHOD FOR PRODUCING HIGH-PURITY TEREPHTHALIC ACID

(71) Applicant: Mitsubishi Gas Chemical Company, Inc., Chiyoda-ku (JP)

(72) Inventors: Goh Nakamura, Kurashiki (JP); Hideaki Fujita, Kurashiki (JP); Kotaro Murakami, Kurashiki (JP)

(73) Assignee: Mitsubishi Gas Chemical Company, Inc., Chiyoda-ku (JP)

( * ) Notice: Subject to any disclaimer, the term of this patent is extended or adjusted under 35 U.S.C. 154(b) by 0 days.

(21) Appl. No.: 15/745,738

(22) PCT Filed: Jul. 21, 2016

(86) PCT No.: PCT/JP2016/071393
§ 371 (c)(1),
(2) Date: Jan. 18, 2018

(87) PCT Pub. No.: WO2017/014264
PCT Pub. Date: Jan. 26, 2017

(65) Prior Publication Data
US 2018/0230078 A1    Aug. 16, 2018

(30) Foreign Application Priority Data

Jul. 22, 2015 (JP) ................................. 2015-144837
Jul. 22, 2015 (JP) ................................. 2015-144838

(51) Int. Cl.
| | |
|---|---|
| C07C 51/43 | (2006.01) |
| C07C 51/265 | (2006.01) |
| C07C 51/487 | (2006.01) |
| C07C 63/26 | (2006.01) |

(52) U.S. Cl.
CPC ............ C07C 51/43 (2013.01); C07C 51/265 (2013.01); C07C 51/487 (2013.01); C07C 63/26 (2013.01)

(58) Field of Classification Search
CPC ....... C07C 51/43; C07C 51/265; C07C 63/26; C07C 51/487
See application file for complete search history.

(56) References Cited

U.S. PATENT DOCUMENTS

| | | | |
|---|---|---|---|
| 5,777,161 A * | 7/1998 | Inary ........................ | C07C 51/42 562/485 |
| 2007/0208191 A1 | 9/2007 | Wonders et al. | |
| 2007/0208192 A1 | 9/2007 | Wonders et al. | |
| 2007/0244340 A1 * | 10/2007 | Wonders ............... | C07C 51/265 562/410 |

FOREIGN PATENT DOCUMENTS

| | | | |
|---|---|---|---|
| CN | 1832914 | * | 9/2006 |
| JP | 55-087744 A | | 7/1980 |
| JP | 57-005797 A | | 1/1982 |
| JP | 57-053431 A | | 3/1982 |
| JP | 09-286758 A | | 11/1997 |
| JP | 09-286759 | * | 11/1997 |
| JP | 09-286759 A | | 11/1997 |
| JP | 10-216501 | * | 8/1998 |
| JP | 10-216501 A | | 8/1998 |
| JP | 2004-250436 A | | 9/2004 |
| WO | 2005/012218 A1 | | 2/2005 |

OTHER PUBLICATIONS

CN1832914 translated (Year: 2006).*
JP09-286759 translated (Year: 1997).*
JP10-216051 translated (Year: 1998).*
International Search Report dated Aug. 23, 2016 in PCT/JP2016/071393, filed on Jul. 21, 2016.

* cited by examiner

*Primary Examiner* — Yevgeny Valenrod
*Assistant Examiner* — Blaine G Doletski
(74) *Attorney, Agent, or Firm* — Oblon, McClelland, Maier & Neustadt, L.L.P.

(57) ABSTRACT

A method for producing high-purity terephthalic acid, comprising following steps (a) to (c):

the step (a); obtaining crude terephthalic acid crystal by liquid phase-oxidizing a p-phenylene compound;

the step (b); obtaining a terephthalic acid crystal slurry by a catalytic hydrogenation treatment of the crude terephthalic acid crystal; and the step (c); introducing the terephthalic acid crystal slurry into an upper portion of a mother liquor replacement tower, and bringing the slurry into contact with an upward flow of replacement water introduced from a bottom portion of the mother liquor replacement tower while making the terephthalic acid crystal settled down in the tower, and extracting the terephthalic acid crystal as a slurry with the replacement water from the tower bottom portion, wherein (1) a stirring blade unit is disposed in a slurry layer in the bottom portion of the mother liquor replacement tower, and fluidity of the slurry layer is maintained by rotating the stirring blade unit in such a way that stirring power is 0.1 to 1.0 kWh/m$^3$ per unit volume of the slurry layer, and

(2) the replacement water is fed through the replacement water feed opening provided in the stirring blade unit.

13 Claims, 2 Drawing Sheets

METHOD FOR PRODUCING HIGH-PURITY TEREPHTHALIC ACID

TECHNICAL FIELD

The present invention relates to a method for producing high-purity terephthalic acid.

BACKGROUND ART

Terephthalic acid is produced by the liquid-phase oxidation reaction of p-phenylene compounds such as p-alkylbenzenes typified by p-xylene, usually by using acetic acid as a solvent, a catalyst such as cobalt or manganese, or a catalyst composed of cobalt or manganese and additionally a promoter such as bromine compounds or acetaldehyde. The liquid-phase oxidation reaction uses acetic acid as a solvent, and the obtained crude terephthalic acid slurry includes, in large amounts, impurities such as 4-carboxybenzaldehyde (4CBA), para-toluic acid (p-TOL) and benzoic acid, or other various coloring impurities. Moreover, the crude terephthalic acid obtained by separating from the crude terephthalic acid slurry also includes these impurities as mixed therein, and thus a considerably higher purification technique is required for the purpose of obtaining high-purity terephthalic acid.

As a method for purifying crude terephthalic acid, there have been known various methods such as the following: crude terephthalic acid is dissolved in acetic acid or water, or mixed solvents of acetic acid and water, at high temperature and under high pressure, and then subjected to a catalytic hydrogenation treatment, a decarbonylation treatment, an oxidation treatment, a recrystallization treatment, or a high-temperature immersion treatment in a slurry condition in which terephthalic acid crystals are partially dissolved. Either in the production of crude terephthalic acid by applying a liquid-phase oxidation reaction, or in the purification of the crude terephthalic acid thus obtained, the operation of separating the terephthalic acid crystals from the dispersion medium is finally required.

Oxidation intermediates such as 4CBA, p-TOL, and benzoic acid, or coloration-causing substances present as impurities in the slurry produced by the oxidation reaction or in the slurry obtained by purification treatment of the crude terephthalic acid are mostly dissolved at high temperature in the slurry dispersion medium; however, when the slurry is cooled to approximately 100° C. to form terephthalic acid crystal-containing slurry, these impurities are incorporated into the terephthalic acid crystals, which makes it difficult to obtain high-purity terephthalic acid.

Accordingly, it is required to separate the dispersion medium under the conditions of high temperature and high pressure, in order to obtain high-purity terephthalic acid from the crude terephthalic acid slurry after the oxidation reaction or the slurry after the purification treatment of the crude terephthalic acid. The most commonly used method for separating the dispersion medium from the terephthalic acid crystal-containing slurry is a centrifugation method; a centrifugation method is widely used for the case of the slurry after the oxidation reaction or the case of the slurry after the purification treatment. The feature of the centrifugation method is such that slurry solution is introduced into a basket rotating at a high speed, the dispersion medium is allowed to overflow from the upper portion of the basket, and the crystals are guided to the bottom of the basket; however, it is known that from the constraints due to the structure and the function of the centrifuge, the continuous operation at high temperature and under high pressure involves some difficulties.

First, because the rinse of crystals during centrifugation or after centrifugation is difficult, the amount of the dispersion medium adhered to the crystals tends to increase; in order to solve this problem, usually adopted is a method in which the centrifuged cakes of the terephthalic acid crystals are again turned into slurry by using a fresh high-temperature solvent. However, the aforementioned method leaves a problem that a plurality of times of separation operations are required to be performed. Moreover, a high speed rotation is performed at high temperature and under high pressure, accordingly the maintenance and the protection of the centrifuge is cumbersome and difficult, the investment for the maintenance and the protection is increased, and thus, the aforementioned method is far from being sophisticated.

As a separation method alternative to a centrifugation method, there has been proposed a dispersion medium replacement apparatus taking advantage of the sedimentation of terephthalic acid crystals due to gravitation. For example, Patent Literature 1 discloses a dispersion media replacement apparatus inside which lateral shelves having a plurality of holes are arranged, and describes the occurrence of the degradation of the efficiency of the replacement due to the channeling or back mixing of the fluid in the apparatus in the case where the apparatus does not have such a structure. In addition, Patent Literature 2 describes the improvement of the replacement performance due to the arrangement of the shelves forming inclined planes in the apparatus.

Patent Literature 3 discloses a method in which acetic acid solvent slurry of terephthalic acid crystals obtained by liquid-phase oxidation of p-alkylbenzene compounds is subjected to a mother liquor replacement with a water solvent slurry, wherein a sedimentary layer of terephthalic acid crystals is formed in the bottom of a mother liquor replacement tower, a stirring blade unit is disposed in the sedimented layer, the stirring blade unit is rotated gently so as to maintain the fluidity in the sedimented layer, the purified terephthalic acid slurry is withdrawn from the bottom portion of the mother liquor replacement tower through a screw conveyor, and additionally replacement water for forming an upward flow of water is fed through a screw conveyor.

CITATION LIST

Patent Literature

Patent Literature 1: Japanese Unexamined Patent Application Publication No. 57-053431
Patent Literature 2: Japanese Unexamined Patent Application Publication No. 55-087744
Patent Literature 3: Japanese Unexamined Patent Application Publication No. 09-286758

SUMMARY OF INVENTION

Technical Problem

However, when such shelves as described in Patent Literature 1 and Patent Literature 2 are arranged in the mother liquor replacement apparatus, sedimentation on the shelves or the obstruction of the openings occurs, thus the stabilization of the operation requires much labor, and the methods described in Patent Literature 1 and Patent Literature 2 are far from being sophisticated techniques.

In the method described in Patent Literature 3, replacement water is fed locally, and hence the channeling of the replacement water tends to occur in the sedimented layer. Moreover, although the fluidity of the sedimented layer is improved by using the mother liquor replacement tower equipped with the stirring blade unit, the slurry is solidified due to the degradation of the fluidity of the sedimented crystals caused by the sliding with the blades in the sedimented layer beneath the stirring blade unit, thus the discharging opening tends to be obstructed by blocking or bridging, and thus the method described in Patent Literature 3 has a drawback of requiring an apparatus such as a screw conveyor in order to withdraw the sedimented terephthalic acid crystal slurry.

In view of the above-described circumstances, an object of the present invention is to provide a method for producing high-purity terephthalic acid in which terephthalic acid crystal slurry after a catalytic hydrogenation treatment of crude terephthalic acid containing solution obtained by liquid phase oxidation of p-phenylene compound is introduced into the upper portion of a mother liquor replacement tower, and the mother liquor replacement is performed by introducing clean water for replacement from the bottom portion of the mother liquor replacement tower, wherein the channeling or back mixing of the fluid in the mother liquor replacement tower is prevented, moreover the solidification and adhesion of the slurry in the slurry layer in the tower bottom portion and the obstruction of the slurry discharging opening are prevented, and accordingly the mother liquor replacement tower is stably operated over a long term.

Solution to Problem

The present inventors performed a continuous diligent study in order to solve the above-described problems, and consequently have discovered that a stirring blade unit is disposed in a bottom portion of a mother liquor replacement tower, a slurry layer in the tower bottom portion is stirred with appropriate stirring power, replacement water is fed through a replacement water feed opening provided in a stirring blade unit or in a ring portion of a ring-shaped sparger, and thus the channeling or back mixing of the fluid is prevented, and an aqueous solution of terephthalic acid crystal slurry after a catalytic hydrogenation treatment can be efficiently subjected to a mother liquor replacement to yield clean water-containing purified terephthalic acid slurry.

Specifically, the present invention is as follows.

[1]

A method for producing high-purity terephthalic acid, comprising following steps (a) to (c):

the step (a); obtaining a crude terephthalic acid crystal by liquid phase-oxidizing a p-phenylene compound;

the step (b); obtaining terephthalic acid crystal slurry by a catalytic hydrogenation treatment of the crude terephthalic acid crystal; and the step (c); introducing the terephthalic acid crystal slurry into an upper portion of a mother liquor replacement tower, and bringing the slurry into contact with an upward flow of replacement water introduced from a bottom portion of the mother liquor replacement tower while making the terephthalic acid crystal settled down in the tower, and withdrawing the terephthalic acid crystal as slurry with the replacement water from the bottom portion, wherein (1) a stirring blade unit is disposed in a slurry layer in the bottom portion of the mother liquor replacement tower, and fluidity of the slurry layer is maintained by rotating the stirring blade unit in such a way that stirring power is 0.1 to 1.0 kWh/m$^3$ per unit volume of the slurry layer, and (2) the replacement water is fed through a replacement water feed opening provided in the stirring blade unit.

[2]

A method for producing high-purity terephthalic acid, comprising following steps (a) to (c):

the step (a); obtaining a crude terephthalic acid crystal by liquid phase-oxidizing a p-phenylene compound;

the step (b); obtaining terephthalic acid crystal slurry by a catalytic hydrogenation treatment of the crude terephthalic acid crystal; and the step (c); introducing the terephthalic acid crystal slurry into an upper portion of a mother liquor replacement tower, and bringing the slurry into contact with an upward flow of replacement water introduced from a bottom portion of the mother liquor replacement tower while making the terephthalic acid crystal settled down in the tower, and withdrawing the terephthalic acid crystal as slurry with the replacement water from the bottom portion, wherein (1) a stirring blade unit and a ring-shaped sparger are disposed in a slurry layer in the bottom portion of the mother liquor replacement tower, and fluidity of the slurry layer is maintained by rotating the stirring blade unit in such a way that stirring power is 0.1 to 1.0 kWh/m$^3$ per unit volume of the slurry layer, and (2) the replacement water is fed through a replacement water feed opening provided in the sparger.

[3]

The production method according to [2], wherein the replacement water is fed simultaneously through the replacement water feed opening provided in the stirring blade unit and through the replacement water feed opening provided in the sparger.

[4]

The production method according to [2] or [3], wherein the replacement water feed opening provided in the sparger is provided so as to feed the replacement water in an oblique downward direction of an outer periphery of the sparger.

[5]

The production method according to any one of [1] to [4], further comprising a step (d); separating the terephthalic acid crystal from the slurry withdrawn from the tower bottom portion.

[6]

The production method according to any one of [1] to [5], wherein a temperature of the replacement water fed through the replacement water feed opening is 5 to 25° C. lower than a temperature of the slurry layer in the tower bottom portion.

[7]

The production method according to any one of [1] to [6], wherein the replacement water feed opening provided in the stirring blade unit is feed opening to feed the replacement water downward, and is arranged at an interval of 20 to 150 mm in each of the stirring blades of the stirring blade unit.

[8]

The production method according to any one of [1] to [7], wherein a plurality of replacement water feed openings are provided in the stirring blade unit, and discharge linear velocity of the replacement water per one of the replacement water feed openings is regulated within a range from 0.1 to 5 m/sec.

Advantageous Effects of Invention

According to the present invention, in the production process of high-purity terephthalic acid using a mother liquor replacement tower, the mother liquor replacement tower can be stably operated in a state of maintaining a high mother liquor replacement rate over a long term.

DESCRIPTION OF EMBODIMENT

Hereinafter, an embodiment for implementing the present invention (hereinafter, simply referred to as "the present embodiment") is described in detail. The following embodiment is presented as exemplification for describing the present invention, and the present invention is not limited to the following contents. The present invention can be implemented as appropriately modified within the range of the gist of the present invention. It is to be noted that in the drawings, the same symbols are allotted to the same elements, and duplicated descriptions are omitted. It is also to be noted that the positional relations such as the left, right, top and bottom are based on the positional relations shown in the drawings unless otherwise specified. It is further to be noted that the dimensional proportions in the drawings are not limited to the dimensional proportions presented in the drawings.

The method for producing high-purity terephthalic acid in the present embodiment is a production method comprising following steps (a) to (c):

the step (a); obtaining a crude terephthalic acid crystal by liquid phase-oxidizing a p-phenylene compound;

the step (b); obtaining terephthalic acid crystal slurry by a catalytic hydrogenation treatment of the crude terephthalic acid crystal; and the step (c); introducing the terephthalic acid crystal slurry into an upper portion of a mother liquor replacement tower, and bringing the slurry into contact with an upward flow of replacement water introduced from a bottom portion of the mother liquor replacement tower while making the terephthalic acid crystal settled down in the tower, and withdrawing the terephthalic acid crystal as slurry with the replacement water from the bottom portion, wherein (1) a stirring blade unit is disposed in a slurry layer in the bottom portion of the mother liquor replacement tower, and fluidity of the slurry layer is maintained by rotating the stirring blade unit in such a way that stirring power is 0.1 to 1.0 kWh/m$^3$ per unit volume of the slurry layer, and (2) the replacement water is fed through a replacement water feed opening provided in the stirring blade unit.

In addition, another method for producing high-purity terephthalic acid in the present embodiment is a production method comprising following steps (a) to (c):

the step (a); obtaining a crude terephthalic acid crystal by liquid phase-oxidizing a p-phenylene compound, the step (b); obtaining terephthalic acid crystal slurry by a catalytic hydrogenation treatment of the crude terephthalic acid crystal, and the step (c); introducing the terephthalic acid crystal slurry into an upper portion of a mother liquor replacement tower, and bringing the slurry into contact with an upward flow of replacement water introduced from a bottom portion of the mother liquor replacement tower while making the terephthalic acid crystal settled down in the tower, and withdrawing the terephthalic acid crystal as slurry with the replacement water from the bottom portion, wherein (1) a stirring blade unit and a ring-shaped sparger are disposed in a slurry layer in the bottom portion of the mother liquor replacement tower, and fluidity of the slurry layer is maintained by rotating the stirring blade unit in such a way that stirring power is 0.1 to 1.0 kWh/m$^3$ per unit volume of the slurry layer, and (2) the replacement water is fed through a replacement water feed opening provided in the sparger.

[Step (a)]

The step (a) is a step of obtaining a crude terephthalic acid crystal by liquid phase-oxidizing a p-phenylene compound.

The step (a) is preferably a step of following a liquid phase oxidation of a p-phenylene compound, obtaining a crude terephthalic acid crystal by separating the reaction mother liquor from the crude terephthalic acid slurry obtained by dropping the pressure and lowering the temperature.

In the present embodiment, the crude terephthalic acid crystal is obtained by the liquid phase oxidation of a p-phenylene compound.

The p-phenylene compound is either a compound having carboxyl groups at the para-positions or a compound having oxidizable substituents to produce carboxyl groups by liquid phase air oxidation at the para-positions, and examples of such a substituent include a methyl group, an ethyl group, a propyl group, an isopropyl group, an aldehyde group and an acetyl group. The substituents may be the same as each other or different from each other.

As the oxidant used in the liquid phase oxidation, oxygen or air is used, and the oxidant is not limited to either one of these; however, air is sufficient when the oxidation is performed in an acetic acid solution, in the presence of a cobalt catalyst and a manganese catalyst and a bromine compound as a co-catalyst. It is preferable to use oxygen when the oxidation is performed in an acetic acid solution in the presence of a cobalt catalyst.

As for the catalyst, when a cobalt catalyst and a manganese catalyst are used, it is preferable to use a bromine compound in combination. A bromine compound is usually regarded as functioning as a co-catalyst, and the bromine compound is particularly preferably hydrogen bromide or sodium bromide. When a cobalt catalyst is used, it is preferable to use acetaldehyde or methyl ethyl ketone as a promoter in combination.

The crude terephthalic acid crystal obtained by the liquid phase oxidation method in an acetic acid solution usually includes many impurities including 4CBA, the value of the OD340, being an index of the whiteness degree, of the crude terephthalic acid crystal is not of a level allowing the crude terephthalic acid crystal to be directly used as polymer raw material for molding. In the present embodiment, there are no particular upper limits for the contents of 4CBA and the other impurities in the crude terephthalic acid crystal. This is also the case for OD340. When the conditions in the liquid phase oxidation step are set to be the conditions that allow the 4CBA content in the crude terephthalic acid crystal to be 500 ppm or more, the combustion loss of acetic acid due to the oxidation reaction tends to be able to be suppressed.

[Step (b)]

The step (b) is a step of obtaining terephthalic acid crystal slurry by a catalytic hydrogenation treatment of the crude terephthalic acid crystal.

The step (b) is preferably a step in which the crude terephthalic acid crystal is dissolved in water at high temperature under high pressure, and then the crude terephthalic acid crystal is subjected to a catalytic hydrogenation treatment; and the obtained reaction liquid is dropped in pressure and lowered in temperature, and thus terephthalic acid crystal slurry is obtained.

In the production method of the present embodiment, the crude terephthalic acid crystal is used in the catalytic hydrogenation treatment step. The catalytic hydrogenation treatment is performed in a state of solution, and accordingly is performed under high-temperature and high-pressure conditions. The temperature in the catalytic hydrogenation treatment is 200° C. or higher, and preferably 240 to 300° C. The concentration of the crude terephthalic acid crystal is preferably within a range from 10 to 40° by weight. The pressure in the catalytic hydrogenation treatment is preferably pressure being sufficient to maintain the liquid phase and being capable of maintaining hydrogen partial pressure appropriate for the catalytic hydrogenation reaction, and is usually preferably within a range from 3 to 10 MPa.

As the catalyst used in the catalytic hydrogenation treatment, the group 8 noble metals are used. As the group 8 noble metals, palladium, platinum, ruthenium, and rhodium are preferable, and in particular, palladium and platinum are preferable. It is to be noted that these metals are not necessarily required to be used each alone, but may be used in combinations of two or more thereof if necessary.

The catalyst is preferably used as supported on a carrier from the viewpoint of the long-term activity maintenance. As the carrier, usually a porous substance is used, carbon-based carriers are preferable with respect to material, and activated carbon, in particular coconut shell activated carbon is preferable. The amount of the catalyst supported on the carrier is not particularly limited because of being effective with a small amount, but is preferably approximately 0.1 to 0.5% by weight in order to maintain long-term activity.

The amount of the hydrogen in the catalytic hydrogenation treatment is preferably two or more times as many as the number of moles of 4CBA contained in the crude terephthalic acid solution. The time used for the catalytic hydrogenation treatment may be substantially time sufficient for the catalytic hydrogenation reaction to proceed, and is usually within a range from 1 to 60 minutes and preferably within a range from 2 to 20 minutes. Usually, the catalytic hydrogenation treatment is performed according to a continuous scheme.

In order to prevent the contamination of fine powders produced by the wear of the activated carbon used as a catalyst carrier, the terephthalic acid solution after the catalytic hydrogenation treatment is, for example, preferably to follow filtration with a strainer made of a sintered titanium, another sintered metal or carbon particles, introduced into a crystallizer having 2 to 6 stages or a batch-type crystallizer which are connected to the strainer serially. Subsequently, the moisture is evaporated by sequentially reducing the pressure, the terephthalic acid crystal is crystallized by lowering the temperature to 120 to 200° C., and thus terephthalic acid crystal slurry is obtained.

[Step (c)]

The step (c) is a step in which the terephthalic acid crystal slurry is introduced into an upper portion of the mother liquor replacement tower, and is brought into contact with an upward flow of replacement water introduced from the tower bottom portion of the mother liquor replacement tower while making the terephthalic acid crystal settled down in the tower, and the terephthalic acid crystal is withdrawn from the tower bottom portion as slurry with the replacement water.

As the terephthalic acid crystal slurry (hereinafter, also referred to as "the feed slurry") introduced into the upper portion of the mother liquor replacement tower, it is preferable to use slurry obtained from the middle stage crystallizer in the multiple stage crystallization step after the catalytic hydrogenation treatment. When the feed slurry is introduced into the mother liquor replacement tower, the temperature of the feed slurry is preferably 120 to 200° C., more preferably 130 to 180° C. and further preferably 140 to 170° C. By regulating the temperature of the feed slurry so as to be within a range from 120 to 200° C., the contamination of impurities into the terephthalic acid crystal is suppressed, and at the same time, the amount of the terephthalic acid dissolved in the mother liquor tends to be able to be reduced.

The terephthalic acid crystal slurry composed of the terephthalic acid crystal and the mother liquor is subjected to the mother liquor replacement step of replacing the mother liquor containing large amounts of impurities with fresh water. The apparatus used in the mother liquor replacement step (namely, "the mother liquor replacement tower") is roughly composed of a tower upper portion, a tower bottom portion and a tower middle portion. The diameter of the tower middle portion can be appropriately changed according to the throughput of the slurry, and is preferably a diameter such that the cross-sectional area of the tower per the throughput of 1 t/hr of the terephthalic acid crystal is 0.2 to 2 $m^2$. The diameter of the tower upper portion and the diameter of the tower bottom portion may be comparable with and can be larger than the diameter of the tower middle portion. The tower upper portion has an introduction unit of feed slurry composed of terephthalic acid crystal and mother liquor. The introduction unit of the feed slurry may be opened on the internal wall of the tower upper portion, preferably be extended and disposed in the tower upper portion, from the viewpoint of achieving satisfactory dispersion of crystals. Moreover, the opening of the feed slurry introduction unit may be directed downward, or the opening may be provided with a structure promoting the dispersion of the crystals such as a dispersion plate. The tower upper portion is further provided with a mother liquor discharging unit, mother liquor substantially containing no terephthalic acid crystal is withdrawn from the mother liquor discharging unit, and the withdrawn mother liquor is guided into a specified treatment tank. The tower bottom portion is provided with a replacement water feed unit, a discharging opening of the purified terephthalic acid slurry having been subjected to the replacement with the replacement water, a regulation unit of the replacement water feed flow rate and the slurry discharging flow rate, and a device of stirring the slurry in the tower bottom portion. The position of the discharging opening of the purified terephthalic acid slurry having been subjected to the replacement with the replacement water is preferably close to the lower region of the tower bottom portion because the slurry has high specific gravity.

A specific example of the operation process of the mother liquor replacement tower is described. The terephthalic acid crystal in the feed slurry introduced into a tower upper portion chamber settles down by gravity through the tower middle portion chamber, and is brought into contact, in a counter-flow manner, with the upward liquid flow of the replacement water introduced from the tower bottom portion. The terephthalic acid crystal having been settled down to the tower bottom chamber is replaced with replacement water to form a slurry layer having a crystal concentration higher than the crystal concentration in the tower middle portion, and is withdrawn from a slurry discharging unit to outside the mother liquor replacement tower.

The pressure of the mother liquor replacement tower is at least pressure capable of maintaining the temperature of the feed slurry and the replacement water. The upper limit of the pressure is free from operational constraints; however, the operation under excessive pressure requires the enhancement of the pressure resistance of the replacement tower to cause an increase in apparatus cost. The pressure of the mother liquor replacement tower is preferably 0.1 to 2 MPa (gauge pressure) and more preferably 0.2 to 1.5 MPa.

The linear velocity of the upward flow of the replacement water in the middle portion of the mother liquor replacement tower is varied depending on the structure of the apparatus, the size of the terephthalic acid crystal or the like, but is preferably 0.2 to 1.5 m/hr (in terms of superficial velocity) and more preferably, 0.5 to 1.0 m/hr. When the linear velocity is too small, the separation of the mother liquor and the terephthalic acid crystal is insufficient, and the purity of the terephthalic acid tends to be degraded. On the other hand, when the linear velocity is too large, the amount used of the replacement water is increased to lead to a drawback.

In this connection, the linear velocity of the upward flow of the replacement water can be calculated from the water balance between the feed amount of the replacement water and the slurry withdrawn from the tower bottom.

It is important to maintain the fluidity of the terephthalic acid crystal slurry layer (hereinafter, also simply referred to as "the slurry layer") in the tower bottom portion of the mother liquor replacement tower. When the slurry layer formed by the sedimentation of the terephthalic acid crystals is in a complete consolidated state, the fluidity as slurry is lost, and it is difficult to withdraw the slurry layer from the mother liquor replacement tower by an engineering technique. In order to prevent such as the difficulty, the slurry layer of the terephthalic acid crystal in the tower bottom portion is required to be kept constantly fluidized. Accordingly, in the present embodiment, a stirring blade unit is disposed in the slurry layer, and moreover, a replacement water feed opening is provided in the stirring blade unit, and thus, the replacement water is fed through the replacement water feed opening as a sprinkler. Alternatively, a stirring blade unit and a ring-shaped sparger are disposed in the slurry layer, and moreover, a replacement water feed opening is provided in the sparger, and thus, the replacement water is fed through the replacement water feed opening. Moreover, replacement water feed openings are provided in the stirring blade unit and in the sparger disposed in the slurry layer, and the replacement water may be fed simultaneously from both of these. Thus, the fluidity of the slurry layer is maintained, and the solidification of the slurry, and the adhesion of crystals to the tower bottom portion or the stirring blade unit can be prevented. In addition, the replacement water is dispersed uniformly in the slurry layer, accordingly the ascent of the replacement water due to the channeling can be prevented, and moreover, there are obtained advantageous effects that the various impurities and the like adhering to the surface of the crystals can be effectively cleaned. On the other hand, when the fluidity of the slurry layer is too high, the interface between the slurry layer in the tower bottom portion and the tower middle portion is disturbed, the purification ability of the mother liquor replacement tower is degraded, and the replacement rate of the mother liquor is lowered. Accordingly, in order to achieve a high mother liquor replacement rate, it is necessary to impart appropriate fluidity to the slurry layer in the tower bottom portion.

The stirring blade unit for imparting appropriate fluidity to the slurry layer in the tower bottom portion may be any stirring blade unit having blades extending from the stirring shaft in a horizontal direction, and the number of the blades and the shapes of the blades are not particularly limited. Examples of the stirring blade unit include blades arranged in a straight line, in the shape of a cross and a comma-shaped design as viewed downward from the top of the stirring shaft. The diameter of the stirring blade unit is not particularly limited as long as the blades each have a length capable of fluidizing the whole of the slurry layer of the terephthalic acid crystal; the diameter of the stirring blade unit is preferably 0.2 to 0.8 times and more preferably 0.3 to 0.7 times as the diameter of the tower bottom portion of the mother liquor replacement tower.

The rotational speed of the stirring blade unit is preferably 0.1 to 20 rpm and more preferably 0.5 to 10 rpm. The power of the stirring blade unit as the power per unit volume of the slurry layer in the tower bottom portion is preferably 0.05 to 1.0 kWh/m$^3$, more preferably 0.1 to 0.8 kWh/m$^3$ and further preferably 0.2 to 0.7 kWh/m$^3$. By regulating the stirring power within a range from 0.05 to 1.0 kWh/m$^3$, appropriate fluidity is imparted to the slurry layer in the tower bottom portion so as to prevent the solidification and adhesion of the slurry and the obstruction of the slurry discharging opening, and at the same time, a high mother liquor replacement rate can be achieved.

The replacement water feed opening provided in the stirring blade unit is preferably provided in such a way that a large number of feed openings are evenly arranged on the whole of the stirring blade unit in order to uniformly disperse the replacement water. The orientation of the replacement water feed opening is not particularly limited, but the replacement water feed opening is preferably provided so as to feed downward the replacement water. Specifically, the feed openings to feed downward the replacement water are provided preferably at an interval of 20 to 150 mm and more preferably at an interval of 40 to 100 mm. By feeding downward the replacement water from the stirring blade unit, the fluidity of the slurry layer is improved, additionally the sliding between the lower part of the stirring blade unit and the terephthalic acid crystal powder in the slurry layer prevents the degradation of the fluidity and the resulting solidification of the powder sedimented in the portion beneath the stirring blade unit, and accordingly neither blocking nor bridging occurs, so as to lower the risk of the obstruction of the discharging opening of the terephthalic acid slurry in the bottom portion of the mother liquor replacement tower.

When the ring-shaped sparger is provided, the ring-shaped sparger is preferably disposed in the interior of the slurry layer of the terephthalic acid crystal and in the position not to interfere with the stirring flow produced by the stirring blade unit, and accordingly the ring-shaped sparger is preferably disposed at a position higher than the stirring blade unit and lower than the interface of the slurry layer. When the operation of the mother liquor replacement tower is continued over a long term, the terephthalic acid crystal possibly firmly adhere and accumulate on the internal wall surface of the mother liquor replacement tower in the slurry layer of the terephthalic acid crystal; when the firmly adhering crystal is exfoliated, the quality of the terephthalic acid crystal is possibly adversely affected. Accordingly, the replacement water feed opening provided in the ring-shaped sparger is preferably disposed so as to feed the replacement water obliquely downward from the outer periphery of the sparger. In the present embodiment, the ring-shaped sparger is provided for the purpose of improving the dispersion of the replacement water in the slurry layer and thus preventing the channeling of the replacement water; the setting of the feed direction of the replacement water in the above-described direction achieves the improvement of the dispersion, the prevention of the channeling, and additionally an extraneous effect that the firm adhesion of the terephthalic acid crystal onto the wall surface can be prevented.

The discharge linear velocity of the replacement water per one replacement water feed opening is preferably 0.1 to 8 m/sec, more preferably 0.1 to 5 m/sec and further preferably 0.5 to 4 m/sec.

The replacement water may be fed to the mother liquor replacement tower at temperature approximately the same as the temperature of the feed slurry fed to the mother liquor replacement tower; however, the temperature of the replacement water is preferably set at lower temperature by 20 to 100° C. than the feed slurry because such the temperature of the replacement water tends to enhance the mother liquor replacement rate. Here, the mother liquor replacement rate is calculated from the removal proportion of the impurities dissolved in the dispersion medium of the feed slurry. In the case where the replacement water feed opening is provided in the stirring blade unit, when the temperature of the replacement water and the temperature of the slurry layer in the tower bottom portion are largely different from each other, the obstruction of the replacement water feed opening and the adhesion and growth of the crystal on the stirring blade unit and the stirring shaft occur, and the mother liquor replacement rate is sometimes gradually degraded during a long-term operation. Accordingly, from the viewpoint of stably maintaining a high mother liquor replacement rate over a long term, the temperature of the replacement water fed from the replacement water feed opening of the mother liquor replacement tower is lower preferably by 5 to 25° C. and more preferably by 6 to 20° C. than the temperature of the slurry layer in the tower bottom portion. The temperature difference between the replacement water and the slurry layer in the tower bottom portion is maintained under 25° C. or less, so that the obstruction of the replacement water feed opening, and the adhesion of the crystal to the stirring blade unit and the stirring shaft tend to be prevented. On the other hand, when the aforementioned temperature difference is 5° C. or more, the mother liquor replacement rate tends to increase.

In order to feed the replacement water from the stirring blade unit, sheath-like conduits for the replacement water are disposed outside the stirring shaft and connected to the hollow stirring blades, and thus, the replacement water is fed through the replacement water feed opening into the interior of the mother liquor replacement tower. It is preferable to use a mechanical seal for the shaft seal in the stirring shaft. The structure involved herein is such that the seal fluid leaks into the sheath-like conduits for the replacement water in the outer periphery of the stirring shaft, and accordingly, the seal fluid to be used is preferably the same water as the replacement water. Moreover, a mechanical seal is used for the shaft seal between the sheath-like conduits for the replacement water and the interior of the mother liquor replacement tower, the replacement water itself is used as the seal fluid, and preferably adopted is a structure allowing the replacement water as the seal fluid, to leak into the interior of the mother liquor replacement tower.

The mother liquor replacement tower in the present embodiment has a structure in which, in the slurry layer in the tower bottom portion of the replacement tower, the terephthalic acid crystal tends to accumulate and remain at the root of the stirring shaft, namely, the central portion of the tower bottom portion of the replacement tower. The remain of the terephthalic acid crystal adversely affects the quality of the product, and accordingly it is preferable to prevent the remain in the root of the stirring shaft by increasing, as described above, the leakage flow of the replacement water in the mechanical seal between the sheath-like conduits for the replacement water and the interior of the mother liquor replacement tower. It is hard to regulate the leakage flow rate of the replacement water optionally, but the rate is preferably regulated within a range from 0.1 to 20% in the total replacement water flow rate.

[Step (d)]

The production method of the present embodiment may further include the step (d) of separating the terephthalic acid crystal from the slurry withdrawn from the tower bottom portion.

The step of separating the terephthalic acid crystal from the slurry withdrawn from the tower bottom portion can separate the terephthalic acid crystal from the slurry, for example, following withdrawing the slurry once into a crystallization tank, feeding the slurry to a solid-liquid separator such as a vacuum filter or a centrifuge. Moreover, the crystal after the separation is fed to a dryer such as a steam tube dryer to dry the crystal, and thus a crystal of high-purity terephthalic acid can be obtained.

EXAMPLES

Hereinafter, the present invention is described more specifically by way of Examples. However, the present invention is not limited by these Examples.

The mother liquor replacement rate in each of following Examples was calculated according to the following formula:

the amount of benzoic acid contained in dispersion medium withdrawn from mother liquor discharging opening in tower top portion/amount of benzoic acid contained as by-product in feed slurry Example 1

The liquid-phase oxidation reaction of p-xylene was performed in acetic acid solution by using a cobalt catalyst and a manganese catalyst, and a co-catalyst of bromide compound, and then crystallization was performed and cooled, and the precipitated crude terephthalic acid crystals were separated. The obtained crude terephthalic acid crystals were dried, and then a catalytic hydrogenation treatment was performed in water as solvent, and thus aqueous solution of terephthalic acid was obtained. Subsequently, the obtained aqueous solution of terephthalic acid was subjected to crystallization to yield terephthalic acid crystal slurry (feed slurry).

Figure 1:
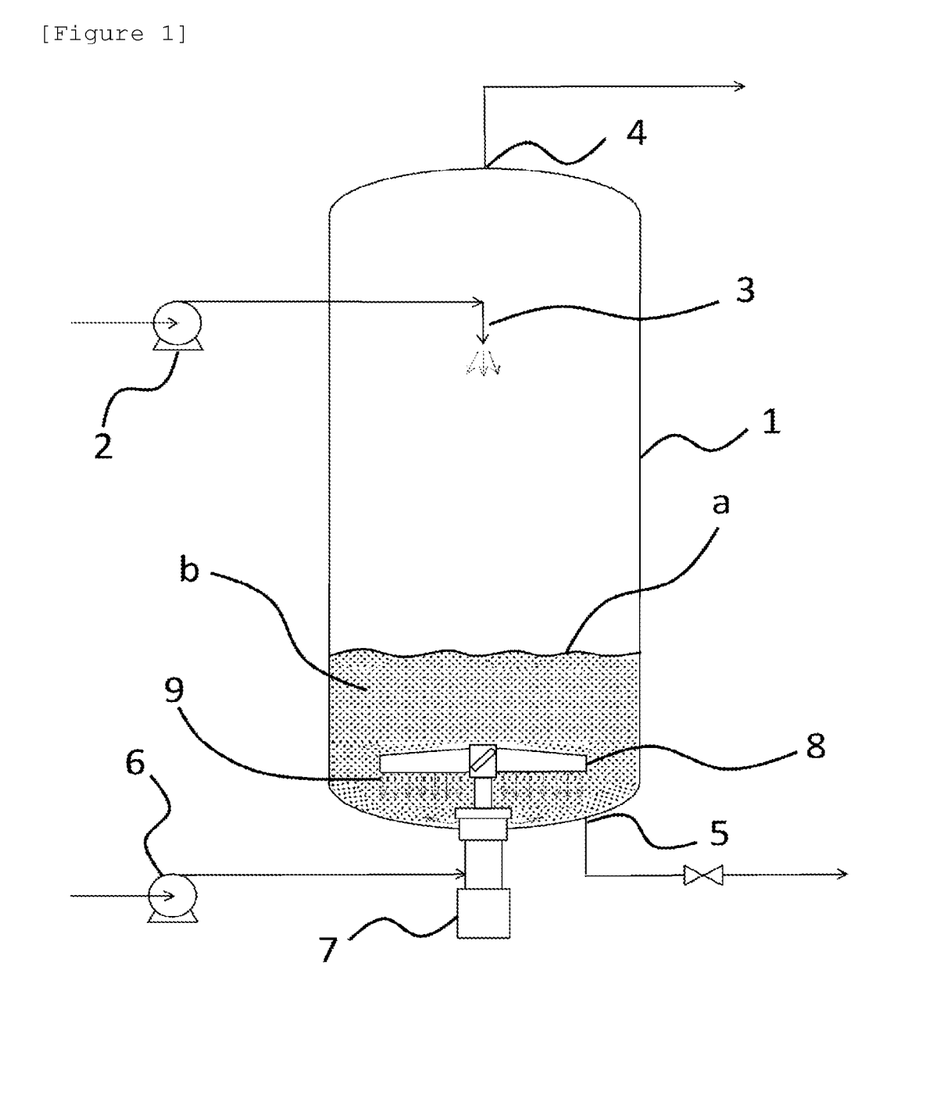
FIG. 1 shows a schematic diagram illustrating a mother liquor replacement apparatus used in Examples.

The operation of replacing the mother liquor of the terephthalic acid crystal slurry (feed slurry) with clean water was performed by using an apparatus shown in FIG. 1. In FIG. 1, the mother liquor replacement tower 1 is a stainless steel vessel, and the tower diameter thereof is 4 m. Feed slurry introducing-nozzle 3 is provided in the upper portion of the mother liquor replacement tower, and is connected to a feed slurry feed pump 2. A mother liquor discharging opening 4 is provided in the tower top portion. The tower bottom portion of the mother liquor replacement tower has a semi-elliptic dish-like structure, and the purified terephthalic acid crystal slurry after the mother liquor replacement treatment is withdrawn through the slurry discharging opening 5. The flow rate of the slurry discharging opening 5 can be regulated by a downstream valve. In the stirring blade unit 8, the diameter of the stirring blade unit is 2 m, and four blades each being tilted by 45 degrees are arranged in a shape of a cross, and replacement water feed openings 9 are evenly arranged at an interval of 70 mm on the back side of each of the stirring blades, in a proportion of 12 feed openings 9 per one blade.

First, a replacement water feed pump 6 was driven, and replacement water at 100° C. was filled into the system through the replacement water feed openings 9. After water started to overflow from the mother liquor discharging opening 4, a motor 7 was operated to rotate the stirring blade unit 8 at a rotational speed of 8 rpm. Next, the feed slurry pump 2 was operated, and feed slurry at 165° C. was fed through the feed slurry-introducing-nozzle 3. While the position of the upper surface 'a' of the sedimentary layer was being detected with a powder surface detector, when the high-concentration slurry layer 'b' in the tower bottom portion reached a predetermined height, the withdrawing of the purified terephthalic acid crystal slurry through the slurry discharging opening 5 was started.

After the system reached a stationary state, the respective flow rates were regulated as follows. When the feed slurry pump 2 was regulated at 108 m$^3$/h (crystal concentration: 32.4%), the slurry discharging opening 5 was regulated at 94 m$^3$/h (crystal concentration: 37.2%), and the replacement water feed pump 6 was regulated at 75 m$^3$/h, the overflow from the mother liquor discharging opening 4 was at approximately 90 m$^3$/h. While monitoring with the powder surface detector so as to maintain that the height of the high-concentration slurry layer 'b' is at a predetermined position, the rotational speed of the stirring blade unit 8 was regulated within a range from 6 to 10 rpm (stirring power: 0.2 to 0.7 kWh/m$^3$). The discharge linear velocity of the replacement water at the replacement water feed openings 9 was 2.45 m/sec. The temperature of the high-concentration slurry layer in the tower bottom portion was 109° C. after establishment of a stable state, and the mother liquor replacement rate was able to be stably maintained within a range from 94% to 96%.

When a continuous operation was allowed to be successively carried out while the height of the high-concentration slurry layer 'b' in the tower bottom portion was being regulated to be constant, the variations from the above-described conditions were small, and a stable operation was able to be performed over a period of approximately half a year.

Example 2

An operation was performed with the same apparatus and in the same manner as in Example 1 except that the temperature of the feed slurry was set to be 195° C. The temperature of the high-concentration slurry layer 'b' in the tower bottom portion was 116° C. after establishment of a stable state, and the mother liquor replacement rate was within a range from 95% to 97%. Under the operation conditions being kept unchanged, continuous operation was allowed to be successively carried out, and a stable operation was able to be performed over a period of approximately half a year.

Example 3

An operation was performed in the same manner as in Example 1 except that the replacement water feed openings 9 were evenly arranged at an interval of 350 mm in a proportion of three openings per one blade. When a stable operation was established, the discharge linear velocity of the replacement water at the replacement water feed openings 9 was 7.35 m/sec. A channeling occurred during operation, and the mother liquor replacement rate was within a range from 91% to 93%.

Comparative Example 1

An operation was performed in the same manner as in Example 1 except that the rotational speed of the stirring blade unit 8 was regulated to be 3 rpm (stirring power: 0.03 kWh/m$^3$), and consequently, the fluidity of the high-concentration slurry layer 'b' was degraded, and the channeling of the upward flow of the replacement water occurred. Moreover, bridging occurred in the tower bottom portion, the withdrawal of the crystals from the tower bottom portion came to be unstable, and consequently the operation was not able to be continued.

Comparative Example 2

An operation was performed in the same manner as in Example 1 except that the rotational speed of the stirring blade unit 8 was regulated to be 15 rpm (stirring power: 2.2 kWh/m$^3$), and consequently, the detection position of the high-concentration slurry layer 'b' came to be unclear. Under the operation conditions being kept unchanged, the operation was continued, and consequently the mother liquor replacement rate was varied within a range from 74% to 82%.

Example 4

An operation was performed in the same manner as in Example 1 except that the replacement water feed openings were provided on the upper end of the stirring blade unit, and the replacement water was fed upward, and consequently the mother liquor replacement rate at the start of the operation was within a range from 93% to 95%. When the operation period of 38 days had passed, the withdrawal of the purified terephthalic acid crystal slurry from the tower bottom portion came to be unstable, and the operation was unable to be continued.

Example 5

An operation was performed in the same manner as in Example 1 except that the temperature of the replacement water fed through the replacement water feed openings was set to be 50° C. The temperature of the high-concentration slurry layer 'b' in the tower bottom portion was 76° C. after establishment of a stable state, and the mother liquor replacement rate was within a range from 95% to 96%. Under the operation conditions being kept unchanged, the continuous operation was allowed to be successively carried out, and consequently after approximately 40 days after the start of the operation, the mother liquor replacement rate gradually decreased, and the replacement rate was not able to be maintained in 94° or more. When 54 days elapsed from the start of the operation, the replacement rate decreased to 90 to 91%, and consequently the operation was terminated. After the termination of the operation, consequently, in the tower bottom portion, the adhesion of large amounts of terephthalic acid crystals to the stirring shaft and the portions of the stirring blades in the vicinity of the stirring shaft, and the obstruction of approximately 60% of the nozzles of the replacement water feed openings 9 were observed.

Example 6

An operation was performed in the same manner as in Example 1 except that the temperature of the replacement water fed through the replacement water feed openings was set to be 150° C. The temperature of the high-concentration slurry layer 'b' in the tower bottom portion was 153° C. after establishment of a stable state, and the mother liquor replacement rate was within a range from 89% to 91%.

Example 7

An operation was performed in the same manner as in Example 2 except that the temperature of the replacement water fed through the replacement water feed openings was set to be 60° C. The temperature of the high-concentration slurry layer 'b' in the tower bottom portion was 88° C. after establishment of a stable state, and the mother liquor replacement rate was within a range from 95% to 97%. Under the operation conditions being kept unchanged, the continuous operation was allowed to be successively carried out, and then after approximately 20 days from the start of the operation, the mother liquor replacement rate gradually decreased, and the replacement rate was not able to be maintained in 94% or more. When 25 days elapsed from the start of the operation, the replacement rate decreased to less than 90°, and consequently the operation was terminated.

After the termination of the operation, consequently, in the tower bottom portion, the adhesion of large amounts of terephthalic acid crystals to the stirring shaft and the portions of the stirring blades in the vicinity of the stirring shaft, and the obstruction of 70% or more of the nozzles of the replacement water feed openings 9 were observed.

Example 8

Figure 2:
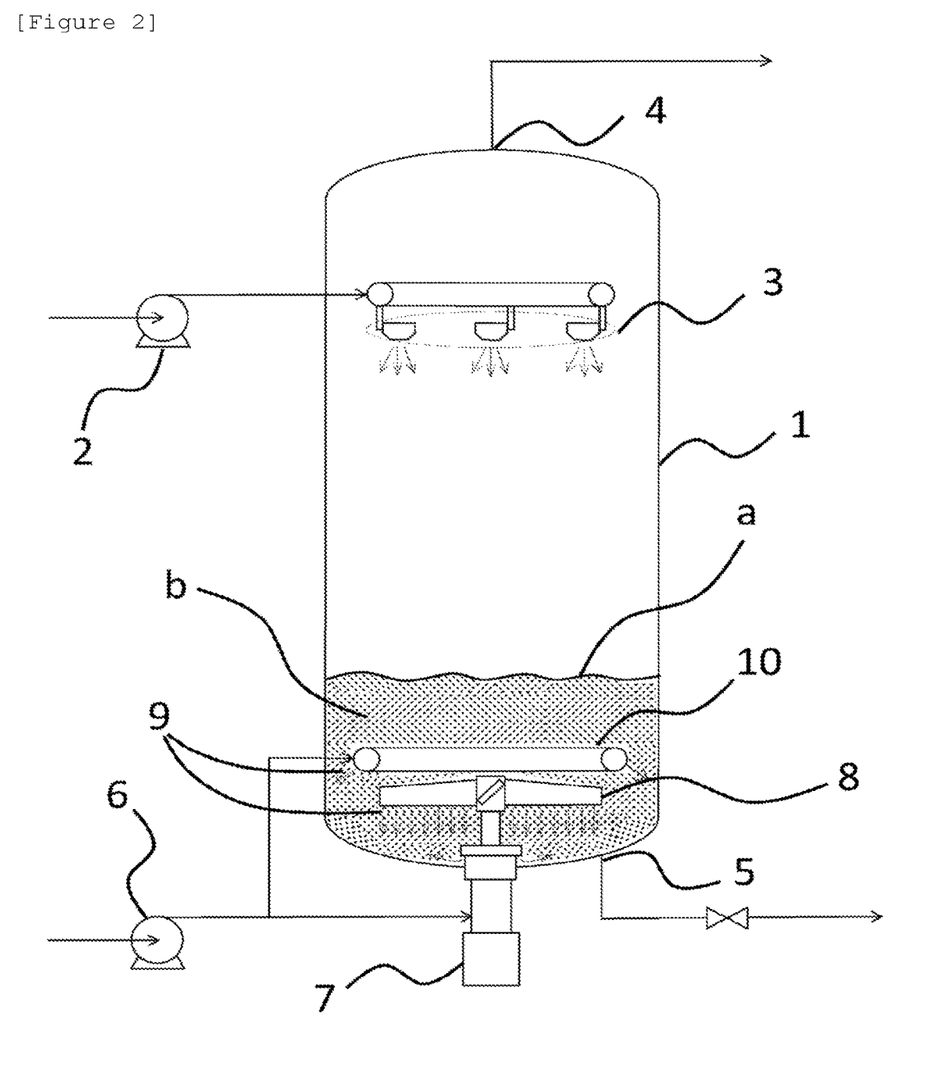
FIG. 2 shows a schematic diagram illustrating another mother liquor replacement apparatus used in Examples.

By using the apparatus shown in FIG. 2, there was performed an operation in which the mother liquor of terephthalic acid crystal slurry was replaced with clean water. In FIG. 2, the mother liquor replacement tower 1 is a stainless steel vessel, and the diameter of the tower is 4 m. Feed slurry introducing-nozzles 3 are provided in the upper portion of the mother liquor replacement tower, and are connected to a feed slurry pump 2. A mother liquor discharging opening 4 is provided in the tower top portion. The tower bottom portion of the mother liquor replacement tower has a semi-elliptic dish-like structure, and a purified terephthalic acid crystal slurry after the mother liquor replacement treatment is withdrawn through the slurry discharging opening 5. The flow rate of the slurry discharging opening 5 can be regulated by a downstream valve. In the stirring blade unit 8, the diameter of the stirring blade unit is 2 m, four blades each being tilted by 45 degrees are arranged in a shape of a cross, and replacement water feed openings 9 are evenly arranged on the back side of each of the stirring blades at an interval of 70 mm, in a proportion of 12 replacement water feed openings 9 per one blade. A ring-shaped sparger is provided at a position approximately 300 mm higher than the upper surface of the stirring blade unit, and in the outer periphery larger than the diameter of the stirring blade unit as viewed from the upper surface side; the replacement water feed openings 9 provided in the sparger are provided so as to feed the replacement water 45-degree obliquely downward from the outer periphery of the sparger. Twenty-four replacement water feed openings are circumferentially evenly arranged.

First, the replacement water feed pump 6 was driven, and the replacement water at 100° C. was fully introduced into the system from the replacement water feed openings 9. When water started to overflow from the mother liquor discharging opening 4, a motor 7 was brought into operation to rotate the stirring blade unit 8 at a rotational speed of 8 rpm. Next, the feed slurry pump 2 was brought into operation to feed the feed slurry at 165° C. from the feed slurry introducing-nozzles 3. When the height of the high-concentration slurry layer 'b' in the tower bottom portion reached the predetermined position while detecting with a powder surface detector, the withdrawal of the purified terephthalic acid crystal slurry through the slurry discharging opening 5 was started.

After the system reached a stationary state, the respective flow rates were regulated as follows. When the feed slurry pump 2 was regulated at 108 m$^3$/h (crystal concentration: 32.4%), the slurry discharging opening 5 was regulated at 94 m$^3$/h (crystal concentration: 37.2%), and the replacement water feed pump 6 was regulated at 75 m$^3$/h, the overflow from the mother liquor discharging opening 4 was at approximately 90 m$^3$/h. The replacement water was fed through the replacement water feed openings of the stirring blade unit at a flow rate of 38 m$^3$/h, and through the feed openings of the ring-shaped sparger at a flow rate of 37 m$^3$/h. While monitoring with the powder surface detector so as to maintain that the height of the high-concentration slurry layer 'b' is at a predetermined position, the rotational speed of the stirring blade unit 8 was regulated within a range from 6 to 10 rpm (stirring power: 0.2 to 0.7 kWh/m$^3$). The discharge linear velocity of the replacement water at the replacement water feed openings 9 was 1.24 m/sec. The temperature of the high-concentration slurry layer in the tower bottom portion was 109° C. after establishment of a stable state, and the mother liquor replacement rate was able to be stably maintained within a range from 95% to 97%.

When a continuous operation was allowed to be successively carried out while the height of the high-concentration slurry layer 'b' in the tower bottom portion was being regulated to be constant, the variations from the above-described conditions were small, and a stable operation was able to be performed over a period of approximately half a year.

Comparative Example 3

An operation was performed in the same manner as in Example 8 except that the rotational speed of the stirring blade unit 8 was regulated to be 3 rpm (stirring power: 0.03 kWh/m$^3$), and consequently, the fluidity of the high-concentration slurry layer 'b' was degraded, and the channeling of the upward flow of the replacement water occurred. Moreover, bridging occurred in the tower bottom portion, the withdrawal of the crystals from the tower bottom portion came to be unstable, and consequently the operation was not able to be continued.

The present application is based on Japanese Patent Applications (Japanese Patent Application No. 2015-144837 and Japanese Patent Application No. 2015-144838) filed at Japan Patent Office on Jul. 22, 2015, and the contents thereof are incorporated herein by reference.

INDUSTRIAL APPLICABILITY

According to the present invention, in the production process of high-purity terephthalic acid using a mother liquor replacement tower, the mother liquor replacement tower can be stably operated in a state of maintaining a high mother liquor replacement rate over a long term.

REFERENCE SIGNS LIST

1: mother liquor replacement tower
2: feed slurry pump
3: feed slurry introducing-nozzle
4: mother liquor discharging opening
5: slurry discharging opening
6: replacement water feed pump
7: motor
8: stirring blade unit
9: replacement water feed opening
10: ring-shaped sparger
a: sedimentary layer upper surface
b: high-concentration slurry layer

The invention claimed is:

1. A method for producing high-purity terephthalic acid, the method comprising:
   obtaining a crude terephthalic acid crystal by liquid phase-oxidizing a p-phenylene compound;
   obtaining a terephthalic acid crystal slurry by a catalytic hydrogenation treatment of the crude terephthalic acid crystal; and
   introducing the terephthalic acid crystal slurry into an upper portion of a mother liquor replacement tower, and bringing the slurry into contact with an upward flow of replacement water introduced from a bottom portion of the mother liquor replacement tower while making the terephthalic acid crystal settle down in the tower, and withdrawing the terephthalic acid crystal as a slurry with the replacement water from the bottom portion,
   wherein
   a stirring blade unit is disposed in a slurry layer in the bottom portion of the mother liquor replacement tower, and fluidity of the slurry layer is maintained by rotating the stirring blade unit in such a way that stirring power is 0.1 to 1.0 kWh/m$^3$ per unit volume of the slurry layer, and
   the replacement water is fed through a replacement water feed opening provided in the stirring blade unit.

2. A method for producing high-purity terephthalic acid, the method comprising:
   obtaining a crude terephthalic acid crystal by liquid phase-oxidizing a p-phenylene compound;
   obtaining a terephthalic acid crystal slurry by a catalytic hydrogenation treatment of the crude terephthalic acid crystal; and
   introducing the terephthalic acid crystal slurry into an upper portion of a mother liquor replacement tower, and bringing the slurry into contact with an upward flow of replacement water introduced from a bottom portion of the mother liquor replacement tower while making the terephthalic acid crystal settle down in the tower, and withdrawing the terephthalic acid crystal as a slurry with the replacement water from the tower bottom portion,
   wherein
   a stirring blade unit and a ring-shaped sparger are disposed in a slurry layer in the bottom portion of the mother liquor replacement tower, and fluidity of the slurry layer is maintained by rotating the stirring blade unit in such a way that stirring power is 0.1 to 1.0 kWh/m$^3$ per unit volume of the slurry layer, and
   the replacement water is fed through a replacement water feed opening provided in the sparger.

3. The method according to claim 2, wherein the replacement water is fed simultaneously through the replacement water feed opening provided in the stirring blade unit and through the replacement water feed opening provided in the sparger.

4. The method according to claim 2, wherein the replacement water feed opening provided in the sparger is provided so as to feed the replacement water in an oblique downward direction of an outer periphery of the sparger.

5. The method according to claim 1, further comprising:
   separating the terephthalic acid crystal from the slurry withdrawn from the tower bottom portion.

6. The method according to claim 1, wherein a temperature of the replacement water fed through the replacement water feed opening is 5 to 25° C. lower than a temperature of the slurry layer in the tower bottom portion.

7. The method according to claim 1, wherein the replacement water feed opening provided in the stirring blade unit is feed opening to feed the replacement water downward, and is arranged at an interval of 20 to 150 mm in each of the stirring blades of the stirring blade unit.

8. The method according to claim 7, wherein a plurality of replacement water feed openings are provided in the stirring blade unit, and discharge linear velocity of the replacement water per one of the replacement water feed openings is regulated within a range from 0.1 to 5 m/sec.

9. The method according to claim 2, further comprising:
   separating the terephthalic acid crystal from the slurry withdrawn from the tower bottom portion.

10. The method according to claim 2, wherein a temperature of the replacement water fed through the replacement water feed opening is 5 to 25° C. lower than a temperature of the slurry layer in the tower bottom portion.

11. The method according to claim 3, wherein the replacement water feed opening provided in the stirring blade unit feeds the replacement water downward, and is arranged at an interval of 20 to 150 mm in each of the stirring blades of the stirring blade unit.

12. The method according to claim 3, wherein a plurality of replacement water feed openings are provided in the stirring blade unit, and discharge linear velocity of the replacement water per one of the replacement water feed openings is regulated within a range from 0.1 to 5 m/sec.

13. The method according to claim 2, wherein the replacement water is fed simultaneously through the replacement water feed opening provided in the stirring blade unit and through the replacement water feed opening provided in the sparger,
   the replacement water feed opening provided in the stirring blade unit feeds the replacement water downward, and
   the replacement water feed opening provided in the sparger is provided so as to feed the replacement water in an oblique downward direction of an outer periphery of the sparger.

* * * * *